(12) United States Patent
Evans et al.

(10) Patent No.: US 10,646,371 B2
(45) Date of Patent: May 12, 2020

(54) INJECTION SYSTEM AND METHOD

(71) Applicant: Salar Surgical Ltd, Pencoed, Bridgend, Mid Glamorgan (GB)

(72) Inventors: Sam Golo Evans, Pencoed (GB); Duncan Fitzsimons, London (GB)

(73) Assignee: Salar Surgical Ltd, Mid Glamorgan (GB)

( * ) Notice: Subject to any disclaimer, the term of this patent is extended or adjusted under 35 U.S.C. 154(b) by 628 days.

(21) Appl. No.: 15/037,939

(22) PCT Filed: Nov. 18, 2014

(86) PCT No.: PCT/GB2014/053402
§ 371 (c)(1),
(2) Date: May 19, 2016

(87) PCT Pub. No.: WO2015/075430
PCT Pub. Date: May 28, 2015

(65) Prior Publication Data
US 2016/0287437 A1 Oct. 6, 2016

(30) Foreign Application Priority Data

Nov. 22, 2013 (GB) .................................. 1320633.9
Sep. 9, 2014 (GB) .................................. 1415908.1

(51) Int. Cl.
*A61F 9/00* (2006.01)
*A61M 5/46* (2006.01)
(Continued)

(52) U.S. Cl.
CPC ...... *A61F 9/0008* (2013.01); *A61B 5/150175* (2013.01); *A61B 5/150656* (2013.01);
(Continued)

(58) Field of Classification Search
CPC ........ A61B 10/0233; A61B 2010/0208; A61B 5/150175; A61B 5/150656;
(Continued)

(56) References Cited

U.S. PATENT DOCUMENTS

2001/0044606 A1  11/2001 Inkpen et al.
2003/0149404 A1*  8/2003 Lehmann .............. A61M 5/326
                                                   604/198
(Continued)

FOREIGN PATENT DOCUMENTS

EP    2500002 A1   9/2012
GB    2252046 A    7/1992
(Continued)

OTHER PUBLICATIONS

ISA/European Patent Office Search Report dated Feb. 26, 2015 in reference to co-pending European Patent Application No. PCT/GB2014/053402 filed Nov. 18, 2014.
(Continued)

*Primary Examiner* — Brandy S Lee
(74) *Attorney, Agent, or Firm* — Dinsmore & Shohl, LLP

(57) ABSTRACT

A device for a hypodermic needle comprises a connector for connecting to a hypodermic needle, a sheath (22) which in use surrounds the hypodermic needle and a biasing device (24) between the connector and the sheath. The sheath is moveable between a first position into which it is biased by the biasing device and a second retracted position against the force of the biasing device, so that in use, the tip of the hypodermic needle is covered in the first position but a defined length of the hypodermic needle is exposed in the second position. The device also sets the position of the angle of the hypodermic needle and locks the sheath over the needle after use.

15 Claims, 13 Drawing Sheets

(51) Int. Cl.
  *A61B 5/15* (2006.01)
  *A61B 10/02* (2006.01)
  *A61M 5/32* (2006.01)

(52) U.S. Cl.
  CPC ....... *A61B 10/0233* (2013.01); *A61M 5/3204* (2013.01); *A61M 5/46* (2013.01); *A61B 2010/0208* (2013.01); *A61F 2009/0052* (2013.01); *A61M 2005/3247* (2013.01); *A61M 2005/3267* (2013.01); *A61M 2210/0612* (2013.01)

(58) Field of Classification Search
  CPC .......... A61F 2009/0052; A61F 9/0008; A61M 2005/3247; A61M 2005/3267; A61M 2210/0612; A61M 5/3204; A61M 5/46; A61M 5/20; A61M 5/326; A61M 2005/2013; A61M 2005/2086; A61M 2205/58; A61M 2205/581; A61M 2205/582; A61M 2205/583; A61M 5/2033; A61M 5/3157; A61M 2005/2073
  See application file for complete search history.

(56) References Cited

U.S. PATENT DOCUMENTS

| | | |
|---|---|---|
| 2006/0015066 A1 | 1/2006 | Turieo et al. |
| 2010/0152646 A1 | 6/2010 | Girijavallabhan et al. |
| 2011/0137261 A1 | 6/2011 | Garber et al. |
| 2013/0253416 A1* | 9/2013 | Rotenstreich ......... A61F 9/0017 604/22 |

FOREIGN PATENT DOCUMENTS

| | | | | |
|---|---|---|---|---|
| GB | 2282069 A * | 3/1995 | | .......... A61M 5/3269 |
| GB | 2282069 A | 3/1995 | | |
| WO | 2008097072 A1 | 8/2008 | | |
| WO | 2010121289 A1 | 10/2010 | | |
| WO | WO-2010121289 A1 * | 10/2010 | | .......... A61M 5/3257 |
| WO | 2012073180 A1 | 6/2012 | | |
| WO | 2013028936 A1 | 2/2013 | | |

OTHER PUBLICATIONS

International Preliminary Report on Patentability dated May 24, 2016 in reference to co-pending International Application No. PCT/GB2014/053402 filed Nov. 18, 2014.

United Kingdom Intellectual Properly Office Examination Report dated Jan. 29, 2019 in reference to co-pending UK Patent Application No. GB1420486.1

Examination Report dated Jul. 19, 2019 in reference to co-pending European Application No. 14819046.5.

* cited by examiner

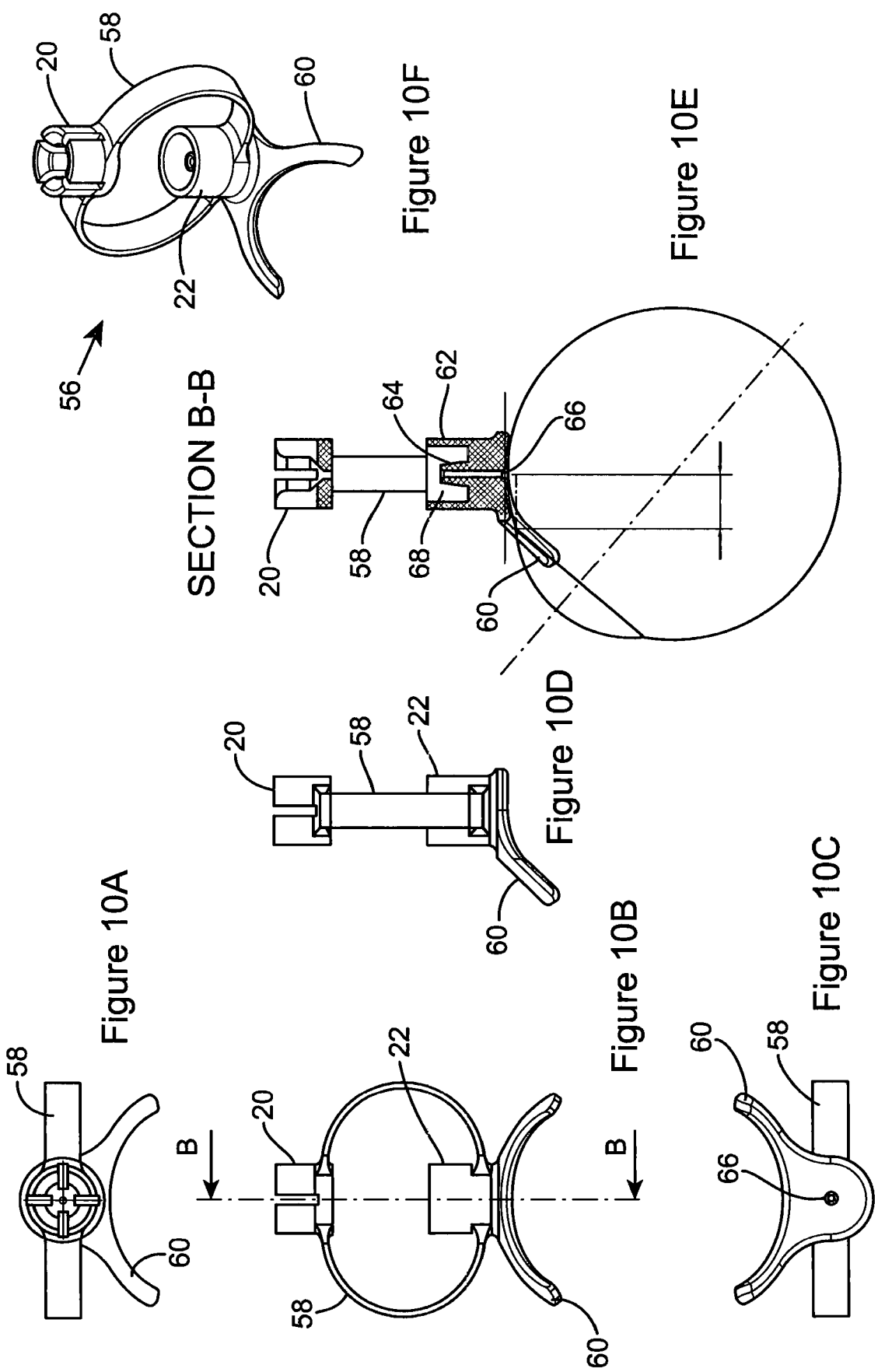

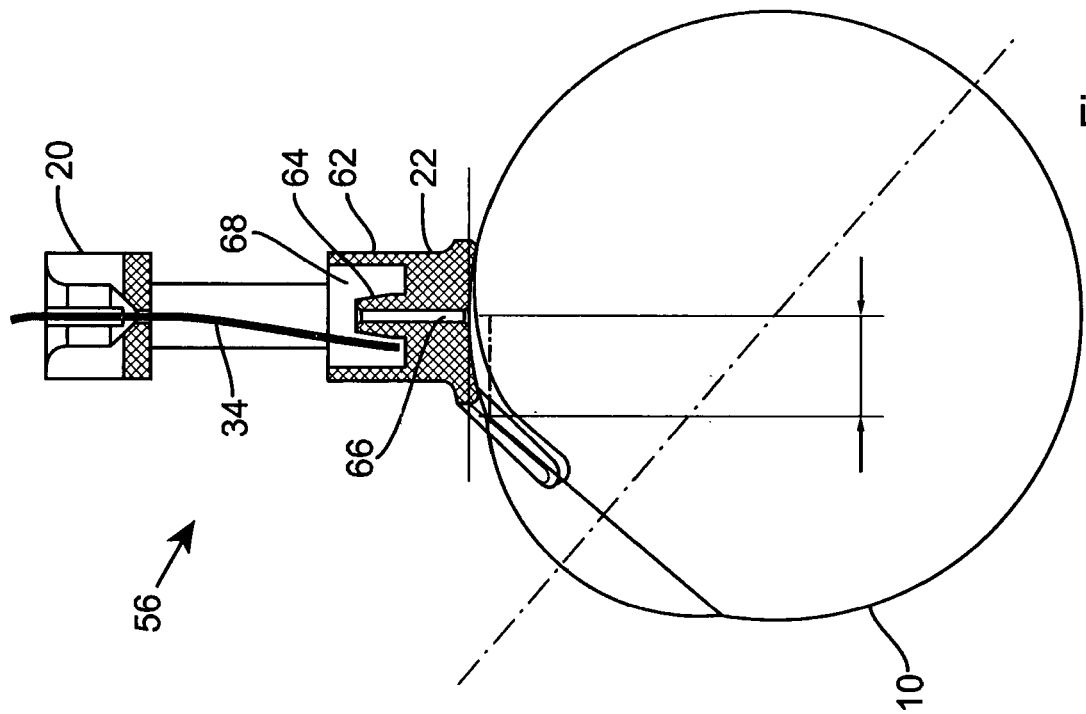
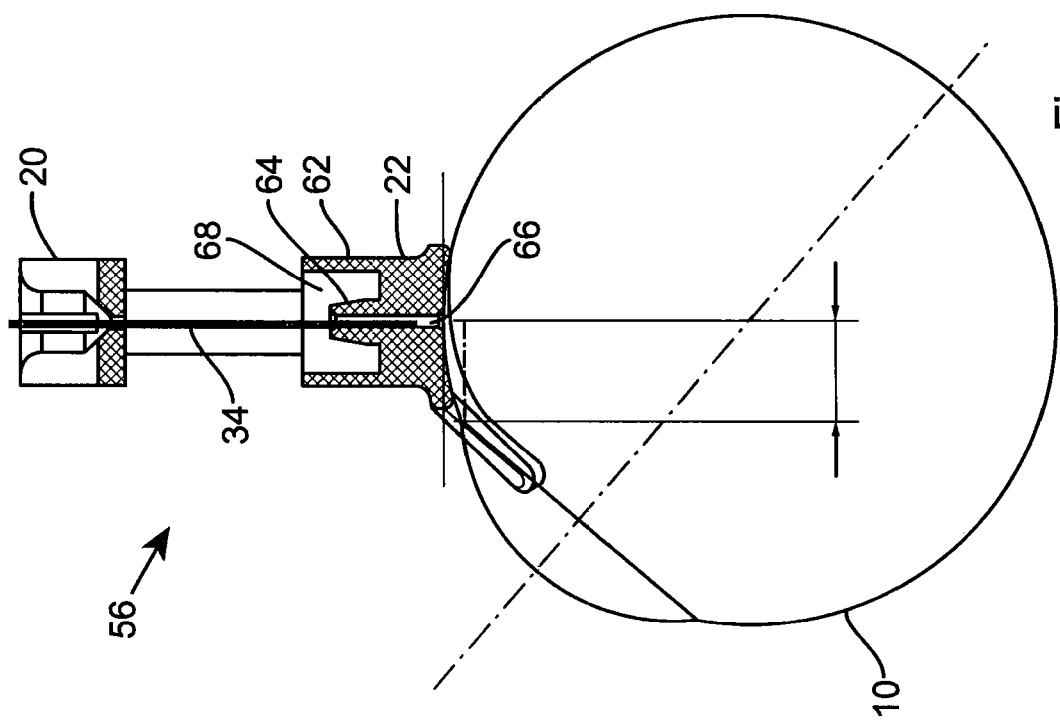

INJECTION SYSTEM AND METHOD

This invention relates to a system for correctly positioning a hypodermic needle and/or ensuring the hypodermic needle is safe after use. The invention also relates to a method for using the system. In particular, the invention relates to a guidance system for injecting therapeutic agents into the eye.

Several eye diseases are treated by injection of therapeutic agents into the vitreous humour in the posterior segment of the eye. Such diseases include, but are not limited to, choroidal neovascular membrane ("wet" macular degeneration), diabetic retinopathy, diabetic maculopathy, macular oedema following retinal vascular disease, infection and inflammation.

Delivery of the therapeutic agent is made via a hypodermic needle and it is important that the position, angle and depth of the injection are correct, to avoid damage to critical ocular structures, including the crystalline lens, intraocular lens implants, the retina and conjunctival blood vessels. Conventionally, this technique is carried out freehand with the use of a caliper marker and the clinician's experience.

A disposable caliper commonly used to align the injection point is shown in FIG. 1. FIG. 1 shows a patient's eye 10 being marked before an injection. The disposable caliper 12 is used to mark an injection point 14 a set distance from the limbus 16 (where the sclera and cornea meet—seen as where the white and coloured parts of the eye meet). The hypodermic needle of a syringe is then placed on the caliper mark and pushed through the conjunctiva and sclera. Once the hypodermic needle has been inserted to the correct depth, the therapeutic agent is injected. Whilst this method marks out the position of the injection, it does not assist in determining the angle and depth of injection. The method requires instruments to be picked up and put down repeatedly, slowing down the process. Furthermore, the sharps used (i.e. hypodermic needle) are not made safe after use.

WO2008/097072 describes a device to aid positioning of a hypodermic needle during intraocular administration of a substance. The device comprises an annular support surface which is placed over the eye with a bore through which a hypodermic needle can be passed, thereby defining the position, angle and depth at which the hypodermic needle penetrates. This device has several disadvantages, including patient discomfort, difficulty of access in deepset eyes (which are very common in this patient group, specifically in elderly patients) and no provision for needlestick safety.

WO2013/028936 describes a needle with a protective sleeve designed to collapse under force, exposing the needle. The sleeve does not return back to an initial position or configuration. The protective sleeve may have a contamination prevention tip with an offset marker to allow precise placement of the needle tip relative to another point. This protective sleeve makes no provision for needlestick safety.

There is a general problem in the field of medicine of needlestick injuries from hypodermic needles. Although hypodermic needles should be disposed of in a 'sharps bin' after use, accidents can still occur, particularly if the hypodermic needle is not disposed of immediately. In particular, where therapeutic agents are administered by patients themselves, the hypodermic needle may not be disposed of properly. Recreational drug users often reuse hypodermic needles. The invention enables a hypodermic needle to be made safe immediately after use.

According to a first aspect of the invention there is provided a device for a hypodermic needle comprising:
 a connector for connecting to a hypodermic needle;
 a sheath which in use surrounds the hypodermic needle;
 and a biasing device between the connector and the sheath;
 wherein the sheath is moveable between a first position into which it is biased by the biasing device and a second retracted position against the force of the biasing device, so that in use, the tip of the hypodermic needle is covered in the first position but a defined length of the hypodermic needle is exposed in the second position.

Preferably the biasing device biases the sheath into the first position after use, thereby covering the tip of the hypodermic needle.

The device therefore provides both a positioning guide by defining the depth of injection and a safety device by covering the tip of the hypodermic needle after use.

The device can be tailored to different length hypodermic needles by selecting the length of sheath and/or biasing device to match, so that the needle is covered in the first position but exposed by a defined length in the second position.

The connector may comprise a connecting hub. The connecting hub may have the size and shape to, in use, fit over a hub of a hypodermic needle. The connecting hub may be conical or frustoconical. The connecting hub may attach to the hub of the hypodermic needle by a friction fit. In one embodiment, the connecting hub is clipped to the hub of the hypodermic needle. In another embodiment the connecting hub may have grooves to allow the secure fitting of ridges commonly found on hypodermic needle hubs. In another embodiment the connecting hub may be bonded to the hypodermic needle hub. In another embodiment, the hub of the device is manufactured to be an integral part of the hub of the needle. The connecting hub may have a central aperture through which, in use, the needle shaft of the hypodermic needle passes. The connecting hub may be made from plastics material. The term hub of a hypodermic needle means the part of a hypodermic needle for connecting to a syringe, for example a Luer connector or push connection.

The biasing device may comprise a spring. The spring may comprise a compression spring. The spring may comprise a coil spring. The coil spring may be positioned so that the needle shaft of the hypodermic needle passes along its longitudinal axis. Alternatively, the spring may comprise a leaf spring. In one embodiment, the spring comprises one or more bow springs, for example two bow springs.

Alternatively, the biasing device may comprise an elastomeric material.

The sheath may comprise a cylindrical tube. The sheath may be positioned so that in use the needle shaft of the hypodermic needle passes through its longitudinal axis. The sheath may comprise a channel, through which in use the hypodermic needle passes. The channel may be aligned with the longitudinal axis.

The device may further comprise a locking device, which locks the sheath over the hypodermic needle after use. The locking device may comprise a member with a first end in a fixed position relative to the sheath and a second end which in an unlocked position can move freely over a surface of the connector but in a locked position is trapped by the connector. The locking device may comprise a member with a first end in a fixed position relative to the sheath and a second end which in an unlocked position lies on an outer surface of the connector and which in a locked position lies on an inner surface of the connector. The member may comprise a leaf spring. The first end of the member may be mounted on an arm mounted on the sheath. Preferably once in the locked position, the locking device cannot be unlocked.

In one embodiment, the arm of the locking device comprises a distance gauge.

In an embodiment, the locking mechanism comprises a recess in the sheath, wherein in an unlocked position the needle passes through a channel in the sheath and in a locked position, the needle rests in the recess. The sheath may comprise a channel, an inner wall and an outer wall and wherein locking device comprises a recess is defined between the inner wall and outer wall. The biasing device may comprise one or more bow springs between the hub and sheath. The device may be put into the locked position by pressing the one or more bow springs to increase the distance between the connecting hub and sheath. Pressing the one or more bow spring in this way will disengage the hypodermic needle from the channel. The outer surface of the inner wall may taper outwards from its upper surface. This shape will encourage the hypodermic needle to enter into the recess.

The device may further comprise a distance gauge to locate the hypodermic needle a set distance from a fixed point. The distance gauge may comprise an arm with one or more distance markers. The arm may be mounted on the sheath. The distance gauge may comprise two or more distance markers, for example first and second distance markers at 3.5 mm and 4.0 mm from the centre of the sheath, respectively. In other embodiments the distance markers may be at different positions depending on the application.

The device may therefore determine the relative position of the sheath from a fixed point. In this way, the position of the hypodermic needle is determined. For example, the device may determine the relative position of the needle from the limbus on an eye.

The device may further determine the angle of the hypodermic needle. The angle of the arm with respect to the sheath may set the angle with respect to a surface on which the arm is located. The angle of the sheath (and therefore the hypodermic needle) can therefore be set with respect to the surface to be injected by positioning the arm against said surface. For example, the device may determine the relative angle of the sheath from the surface of an eye. The arm may describe a curve similar to that of the scleral surface in order to appose the surface fully. Alternatively it may be less than the curvature of the sclera, or straight. The arm may be canted at an angle from the sheath to allow for injection of the needle perpendicular to the scleral surface at the point of injection, for example the angle between the sheath and the arm may be in the range between 70 and 90 degrees. The arm may be constructed from a material, and in such a way, to minimise discomfort to the patient, for example with a broad base (e.g a width of 0.5–2.0 mm), or with absorbent material, such as a closed cell foam. Additionally the arm and lower surface of the sheath may be constructed to minimise slippage on the conjunctiva, for example with dimples or ridges to grip the surface of the eye.

The device may be for the delivery of therapeutic agents to the eye, or other anatomical locations.

The device may be for the removal of samples of tissue or fluid for treatment or biopsy.

The device may further comprise a hypodermic needle.

The device may be integral with the hypodermic needle.

A second aspect of the invention provides a device comprising:
 a hypodermic needle with a connector;
 a sheath which surrounds the hypodermic needle;
 and a biasing device between the connector and the sheath;
 wherein the sheath is moveable between a first position into which it is biased by the biasing device wherein the tip of the hypodermic needle is covered and a second retracted position against the force of the biasing device wherein a defined length of the hypodermic needle is exposed.

A third aspect of the present invention provides a method for positioning a syringe with hypodermic needle for delivery of a therapeutic agent to a body part or removal of samples of tissue or fluid from the body part using a device, comprising the steps of:
 placing sheath of the device onto the desired position on the surface of the body part;
 pushing syringe downwards so that sheath is displaced against the biasing device from its first position relative to the hypodermic needle to its second position, whilst remaining on the surface of the body part so that the hypodermic needle enters the body part by a predetermined distance;
 injecting contents of syringe into body part or removing of samples of tissue or fluid; and
 removing syringe and hypodermic needle from body part.

The body part may be selected from the group of an eye, skin on the torso and a body part around a tumor. The body part may comprise any body part where the position and depth of delivery of therapeutic agents is important.

The method may comprise the additional step of:
 placing the distance gauge of the device on a fixed location on the body part, to thereby correctly position the sheath. The fixed location may include anatomical features on the body part or markings made by a health worker, for example following medical imaging, such as X-rays, MRI etc.

The method may comprise the additional step of:
 resting the arm of the distance gauge on the surface of the body part to thereby correctly set the angle of the sheath.

The method may comprise the additional step of:
 after use, allowing the sheath to return downwards under the force of the biasing device, thereby covering the tip of the needle.

A fourth aspect of the present invention provides a method for positioning a syringe with hypodermic needle for delivery of therapeutic agents to the eye or removal of samples of tissue or fluid from the eye using a device, comprising the steps of:
 placing sheath of device onto desired position on surface of eye;
 pushing syringe downwards so that sheath is displaced against the biasing devices from the first position relative to the hypodermic needle to the second position, whilst remaining on the surface of the eye so that the hypodermic needle enters the eye by a predetermined distance;
 injecting contents of syringe into eye or removal of samples of tissue or fluid from the eye; and
 removing syringe and hypodermic needle from eye.

The method may comprise the additional step of:
 placing the distance gauge of the device on the limbus of the eye, to thereby correctly position the sheath.

The method may comprise the additional step of:

resting the arm of the distance gauge on the surface of the eye to thereby correctly set the angle of the sheath.

The method may comprise the additional step of:

after use, allowing the sheath to return downwards under the force of the biasing device, thereby covering the tip of the needle.

According to a fifth aspect of the invention there is provided a safety device for a hypodermic needle comprising:

a connector for connecting to a hypodermic needle;
a sheath which in use surrounds the hypodermic needle;
a biasing device between the connector and the sheath;
wherein the sheath is moveable between a first position into which it is biased by the biasing device and a second retracted position against the force of the biasing device, so that in use, the tip of the hypodermic needle is covered in the first position but exposed in the second position; and
a locking device which locks the sheath in the first position after use.

According to a sixth aspect of the invention there is provided a hypodermic needle comprising:

a hypodermic needle shaft;
a hub for connecting to the hypodermic needle shaft to a syringe;
a connector for connecting to the hypodermic needle shaft or the hub;
a sheath which in use surrounds the hypodermic needle shaft;
a biasing device between the connector and the sheath;
Wherein the sheath is moveable between a first position into which it is biased by the biasing device and a second retracted position against the force of the biasing device, so that in use, the tip of the hypodermic needle shaft is covered in the first position but exposed in the second position; and
a locking device which locks the sheath in the first position after use.

The locking device may comprise a member with a first end in a fixed position relative to the sheath and a second end which in an unlocked position can move freely over a surface of the connector but in a locked position is trapped by the connector.

The locking device may comprise a member with a first end positioned in a fixed position relative to the sheath and a second end which in an unlocked position lies on an outer surface of the connector and which in a locked position lies on an inner surface of the connector. The member may comprise a leaf spring.

In one embodiment, the first end of the member is fixed on an arm mounted on the sheath.

In an embodiment, the sheath comprises a channel and the locking mechanism comprises a recess in the sheath, wherein the locking device comprises a recess between channel and outer wall, wherein in an unlocked position the needle passes through the channel and in a locked position, the needle rests in the recess. The sheath may comprise an inner wall around the channel and an outer wall and wherein the recess is defined between the inner wall and outer wall. The biasing device may comprise one or more bow springs between the hub and sheath. The outer surface of the inner wall may taper outwards from its upper surface.

According to a seventh aspect of the invention there is provided a device for a hypodermic needle comprises:

a connector for connecting to a hypodermic needle;
a sheath comprising a channel and a recess;
and a biasing device between the connector and the sheath, biasing the sheath away from the connector;
wherein in use, in an unlocked position, the hypodermic needle passes through the channel of the sheath and in a locked position, the hypodermic needle is located in the recess between the inner and outer walls of the sheath.

In the unlocked position, the sheath may cover the needle unless a force is applied to the sheath against the bias of the biasing device.

The biasing device may comprise a spring, for example a coil, leaf or bow spring. In one embodiment, the spring comprises two or more bow springs.

The device may comprise a gauge to set at least one of the position and angle of the hypodermic needle. The gauge may be mounted on the sheath. The gauge may set the position of the hypodermic needle a set distance from a fixed location. The gauge may set the angle of the hypodermic needle.

According to a eighth aspect of the invention there is provided a method for locking a safety device over the tip of a hypodermic needle, the safety device comprising a connector connected to a hypodermic needle, a sheath comprising a channel through which the hypodermic needle and recess and a biasing device between the connector and the sheath, the method comprising:

pushing the sheath away from the connector to disengage the hypodermic needle from the channel of the sheath;
releasing the sheath, allowing the hypodermic needle to enter the recess in the sheath.

The method may comprise moving the sheath transversely to the connecting hub, so that the hypodermic needle is misaligned with the channel.

In one embodiment the biasing device comprises one or more bow spring, each bow spring having a convex surface and the step of pulling the sheath away from the connector comprises pressing the convex surface of the one or more bow spring. The biasing device may comprise two bow springs substantially opposite one another with their convex surfaces facing outwards and the step of pushing the sheath away from the connector may comprise pressing the convex faces of the bow springs.

Preferably, once in the locked position, the locking device cannot be unlocked.

The connector may comprise an integral part of a hypodermic needle. Alternatively, the connector may fit onto a hypodermic needle, for example onto the connecting hub of a hypodermic needle.

The device is suitable for use in injecting body parts other than the eye, for example subcutaneous, intra-articular or transcutaneous injections. In particular it is suitable for targeted tumor injections.

Throughout the description and claims of this specification, the words "comprise" and "contain" and variations of the words, for example "comprising" and "comprises", mean "including but not limited to", and do not exclude other components or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, characteristics or steps described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

The present invention will now be further described with reference to the following non-limiting examples and the accompanying illustrative drawings, of which:

FIGS. 10A-10F illustrate a further embodiment of the device; and

FIGS. 11A-11B illustrate the embodiment of FIGS. 10A-10F in use.

Figure 1:
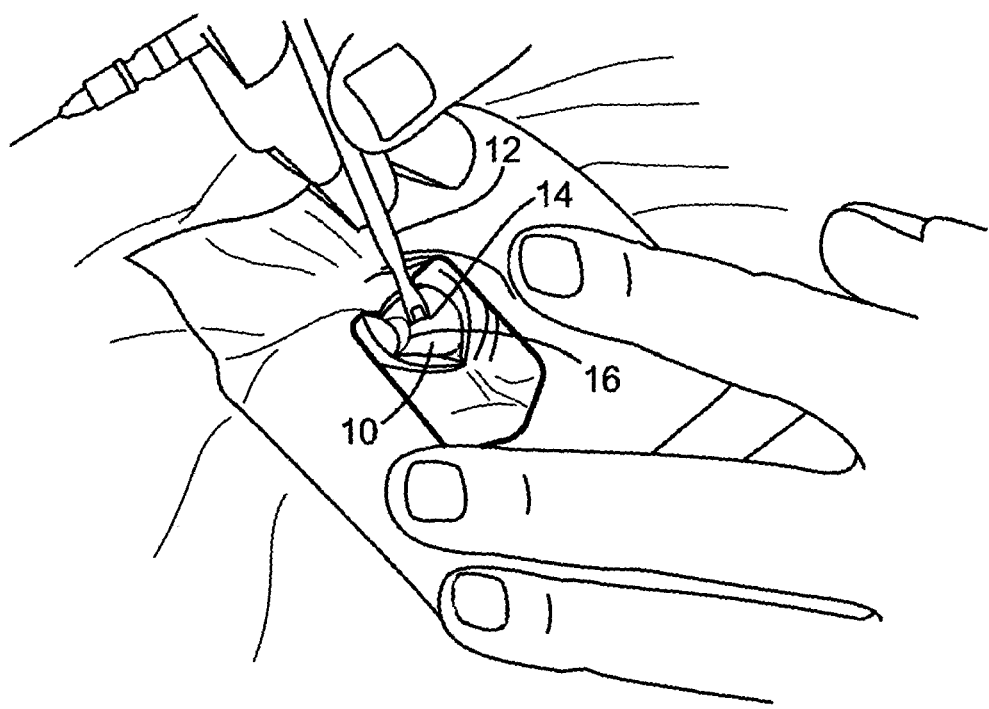
FIG. 1 illustrates a prior art method of marking the correct position prior to injection.
Figure 2:
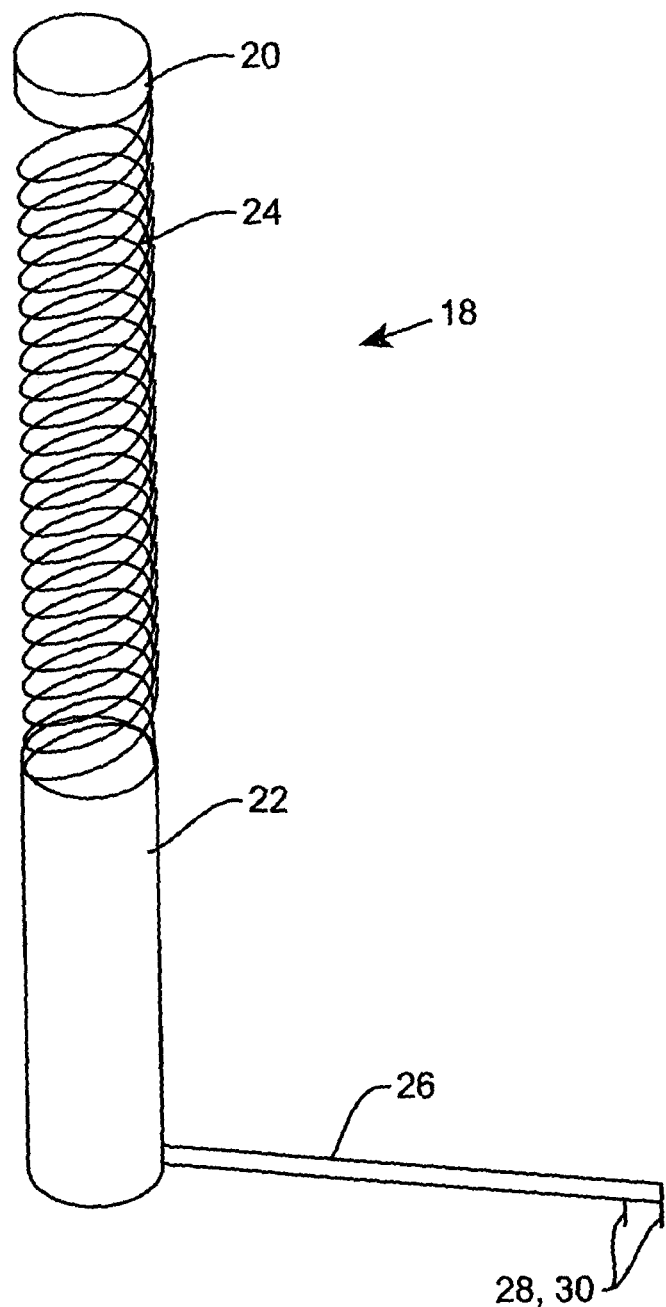
FIG. 2 is a schematic illustration of the invention.

FIG. 2 illustrates the device of the invention. The device 18 comprises a connecting hub 20 for connecting to a hub of a hypodermic needle, a sheath 22 and a coil spring 24 disposed between them. The sheath 22 and spring 24 are dimensioned so that the shaft of a hypodermic needle can pass through their centers, with the internal diameter of the sheath being greater than the external dimension of the hypodermic needle.

Mounted on the sheath 22 is an arm 26 extending laterally from the longitudinal axis of the sheath. The arm is provided with two distance gauges 28, 30 a pre-defined distance from the centre of the sheath.

Figure 3:
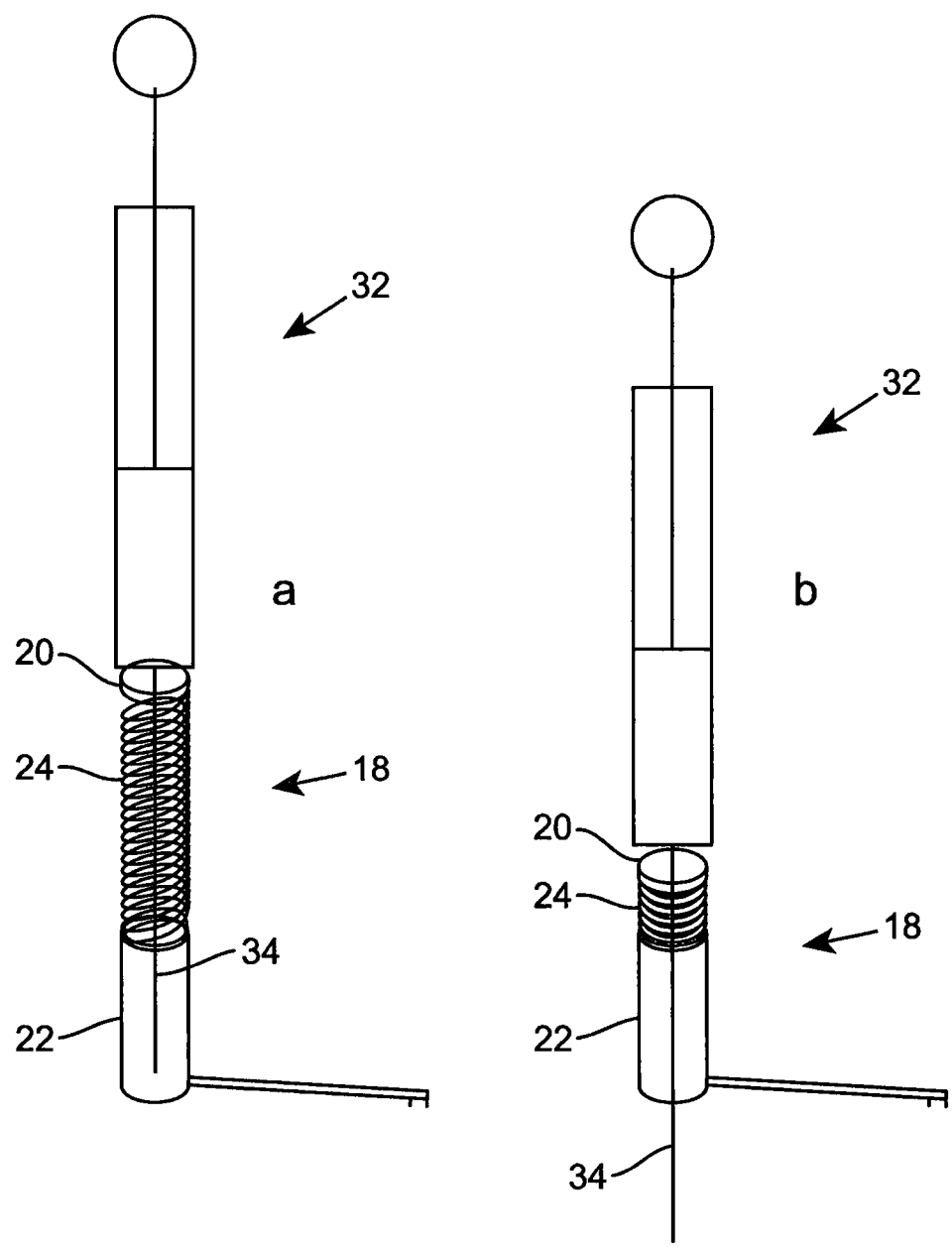
FIGS. 3A and 3B illustrate the embodiment of FIG. 2 mounted on a syringe in two positions.

FIGS. 3A and 3B show the device 18 mounted on a syringe 32 and hypodermic needle 34. The connecting hub 20 is mounted on the hub of the hypodermic needle 18 (not shown) and the hypodermic needle extends along the longitudinal axis of the spring and sheath. When no force is exerted onto the spring, the hypodermic needle 34 is fully enclosed within the device, as shown in FIG. 3A. However, when the spring 24 is compressed, the hypodermic needle 34 extends out from the bottom of the sheath 22. When the spring 24 is fully compressed between the connecting hub 20 and sheath 22, the hypodermic needle 34 will protrude out from the sheath 22 by a fixed amount.

The arrangement of the connector, spring and sheath ensures that sharp needle point of the hypodermic needle is protected when the device is not in use, protecting healthcare workers and patients from the danger of accidental injury by the needle point. During use, the travel of the needle into the eye is limited by the sheath, ensuring that the needle point does not advance too deeply into the eye and cause damage to delicate ocular structures.

Figure 4:
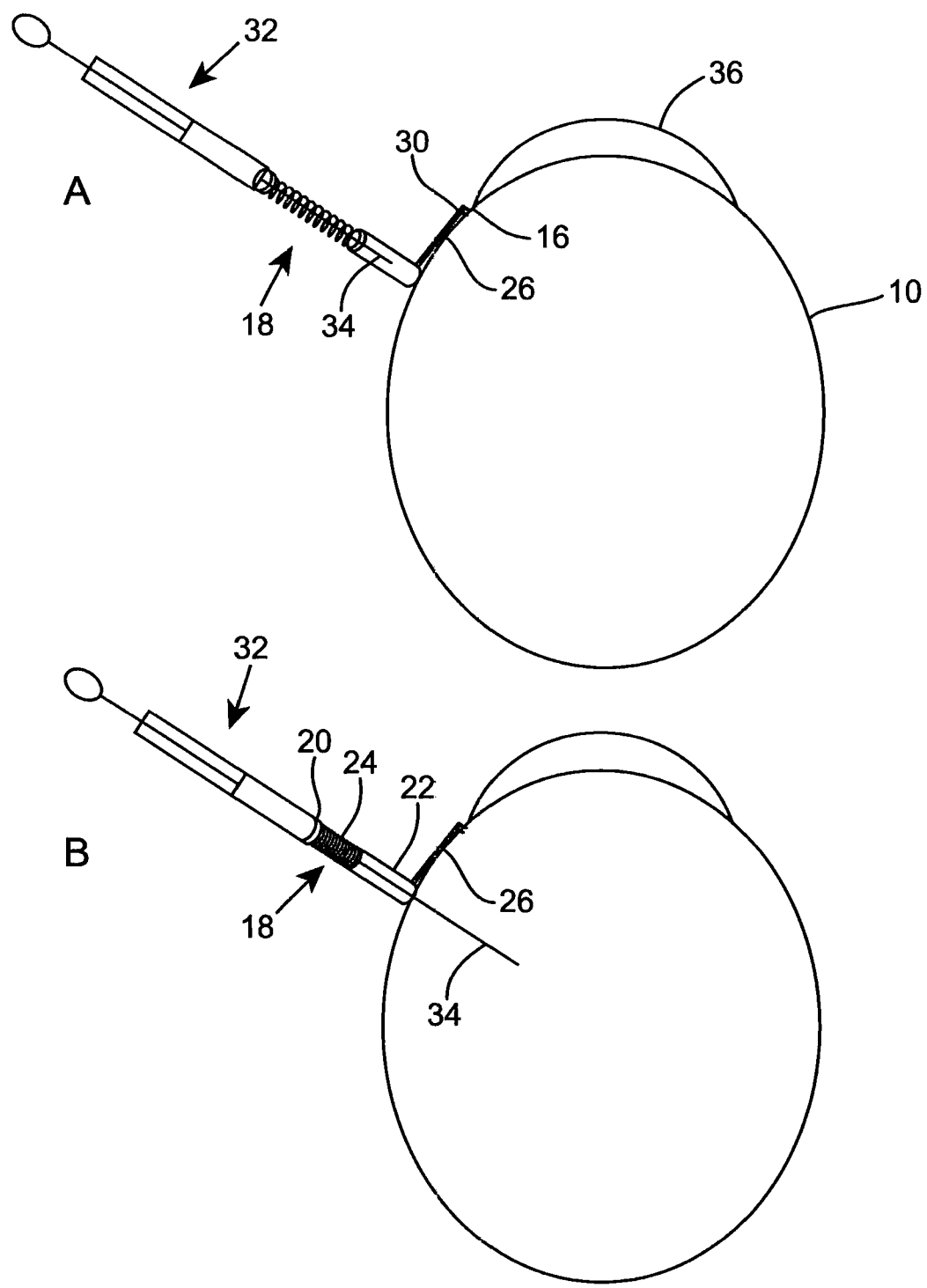
FIGS. 4A and 4B show sectional views of the device correctly positioning a syringe on an eye.

FIG. 4 shows the device in use to correctly position a hypodermic needle of a syringe on an eye prior to administering a therapeutic agent into the vitreous humour in the posterior segment of the eye. FIG. 4A illustrates a cross section of an eye 10 from above showing the corner 36. A syringe 32 and hypodermic needle 34 with device 18 attached is shown lined up on the eye prior to an injection. The distance gauge 30 is aligned with the limbus 16 (the boundary between the white and coloured parts of the eye) so that by positioning arm 26 radially from the limbus, the sheath is positioned a set distance away. The arm 26 is laid onto the surface of the sclera and thereby sets the angle of the sheath. The angle of the sheath (and thereby hypodermic needle) with respect to the sclera at the point of entry should be in the range of 70-90 degrees, preferably 90 degrees.

Once the position and angle of the sheath have been set by means of arm 26 and distance gauge 30, the hypodermic needle 34 may be inserted into the eye as shown in FIG. 4B. Whilst the sheath rests on the surface of the eye, the syringe 32 is pushed downwards compressing the spring 24 between the hub 20 and the sheath 22. During this motion, the hypodermic needle 34 is pushed into the eye for a fixed distance (i.e. when the spring is fully compressed), whilst the positioning guide (including the sheath) remains on the outside of he eyeball. The hypodermic needle 32 has now been inserted into the eye at a set position, angle and depth. In this correct position, the drug may be injected into the vitreous humour without damaging any structures of the eye.

Figure 5:
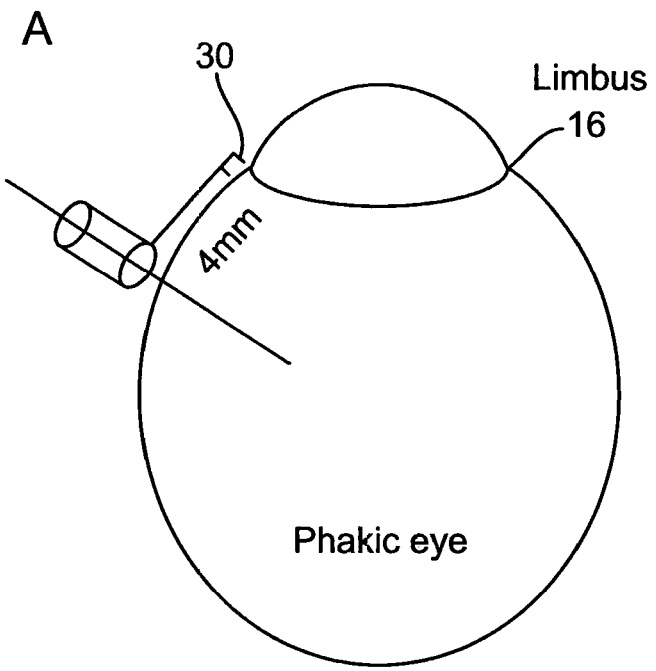
FIGS. 5A and 5B show the device allowing different positions for phakic and pseudophakic eyes respectively.
FIGS. 5C and 5D show an alternative embodiment of the device allowing different positions for phakic and pseudophakic eyes respectively.
Figure 5:
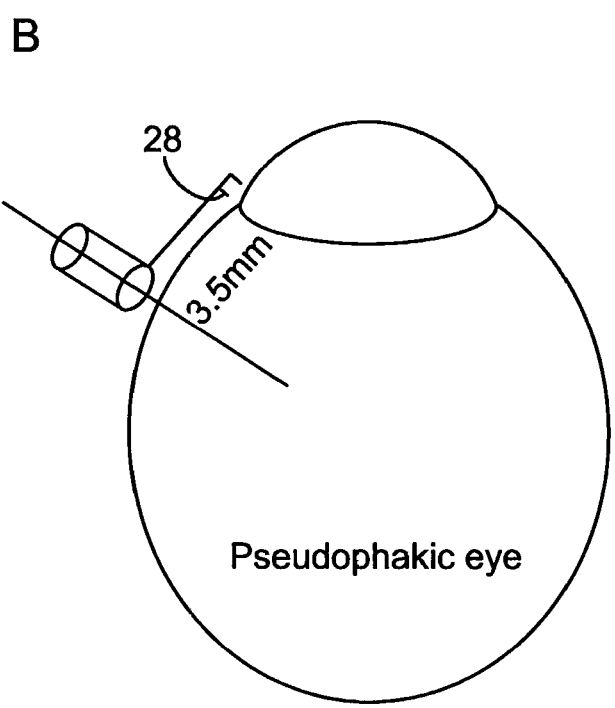

An eye may be phakic (containing its natural crystalline lens) as illustrated in FIG. 5A or pseudophakic (when the natural lens has been removed and replaced by an artificial lens) as illustrated in FIG. 5B. In these two cases, the position of the injection is different; 4 mm from the limbus in a phakic eye and 3.5 mm from the limubs in a pseudophakic eye. The device is provided with two distance markers 28, 30 on the distance gauge which define these two distances from the centre line of the sheath. In FIG. 5A, the outer distance marker 30 is shown aligned with the limbus, thereby positioning the sheath centre line 4 mm away. In FIG. 5B, the inner distance marker 28 is shown aligned with the limbus, thereby positioning the sheath centre line 3.5 mm away.

Figure 5C:
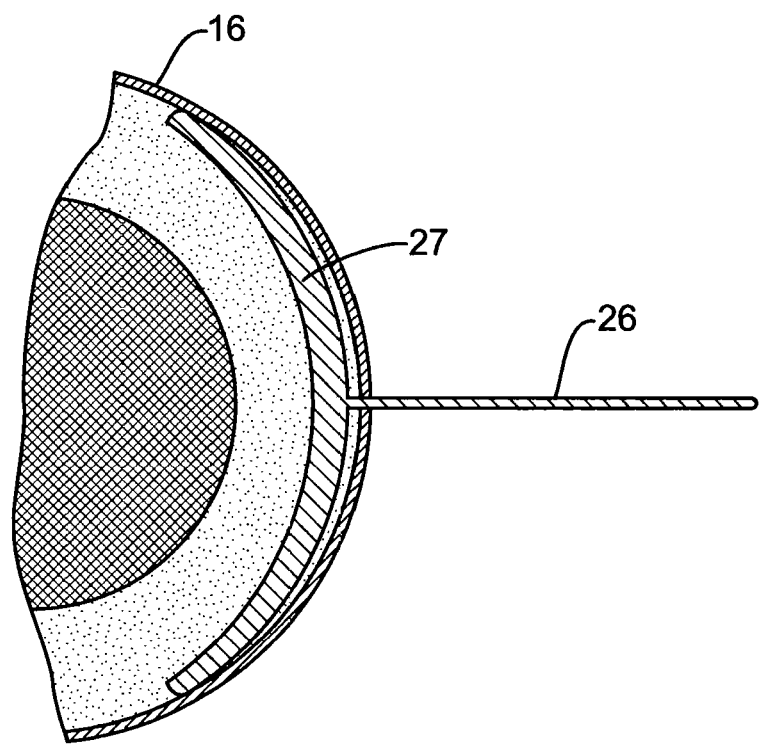
Figure 5D:
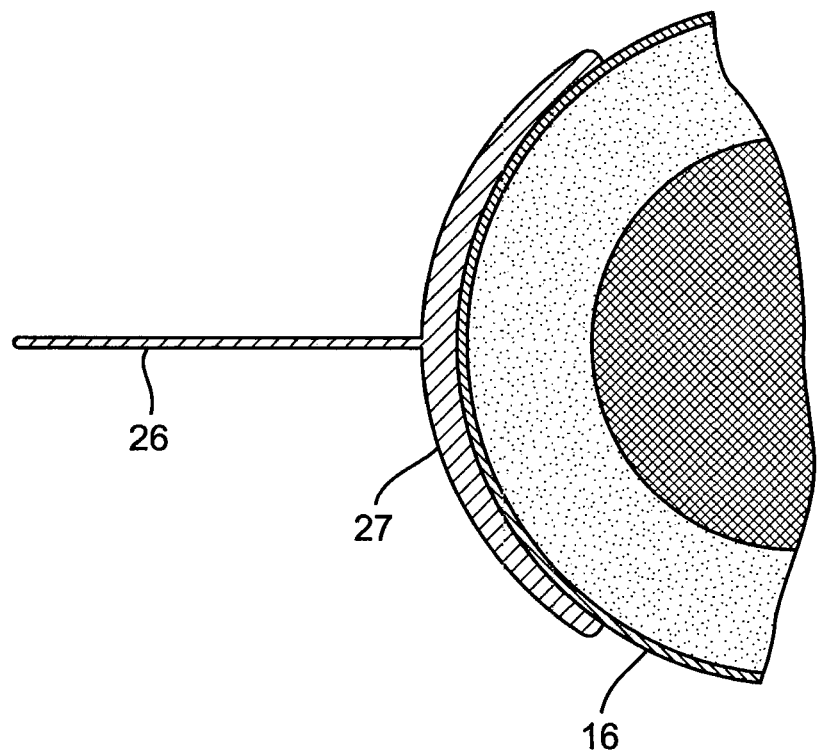

An alternative embodiment of the distance gauge is shown in FIGS. 5C and 5D. In this embodiment the free end of the distance gauge 26 has a C-shaped tip 27 with a radius of curvature similar or equal to that of the limbus of the eye. The distance along the distance gauge from the centre of the sheath to the outer circumference of the C-shaped tip is 3.5 mm, whilst the centre of the sheath to the inner circumference of the C-shaped tip is 4.0 mm Therefore, the same distance gauge may be used on either a phakic eye or pseudophakic eye by aligning either the outside or inside of the C-shaped tip to the limbus. FIG. 5C shows the external circumference of the C-shaped tip 27 being aligned with the limbus, whilst FIG. 5D shows the internal circumference of the C-shaped tip 27 being aligned with the limbus.

Figure 6:
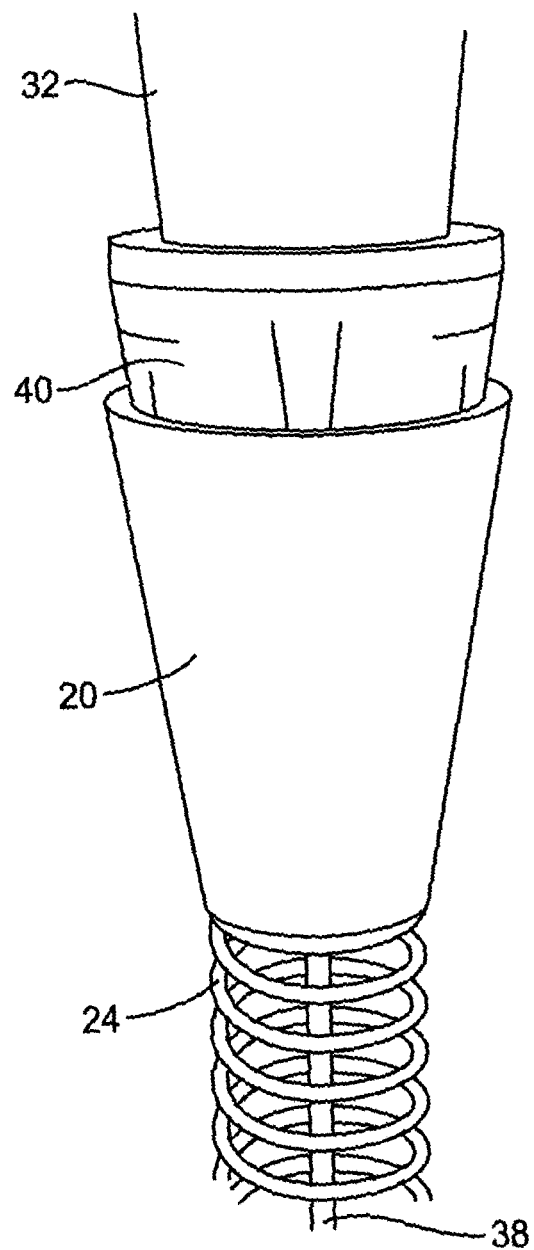
FIG. 6 is a side view illustrating connection of the device onto a hypodermic needle.
Figure 7:
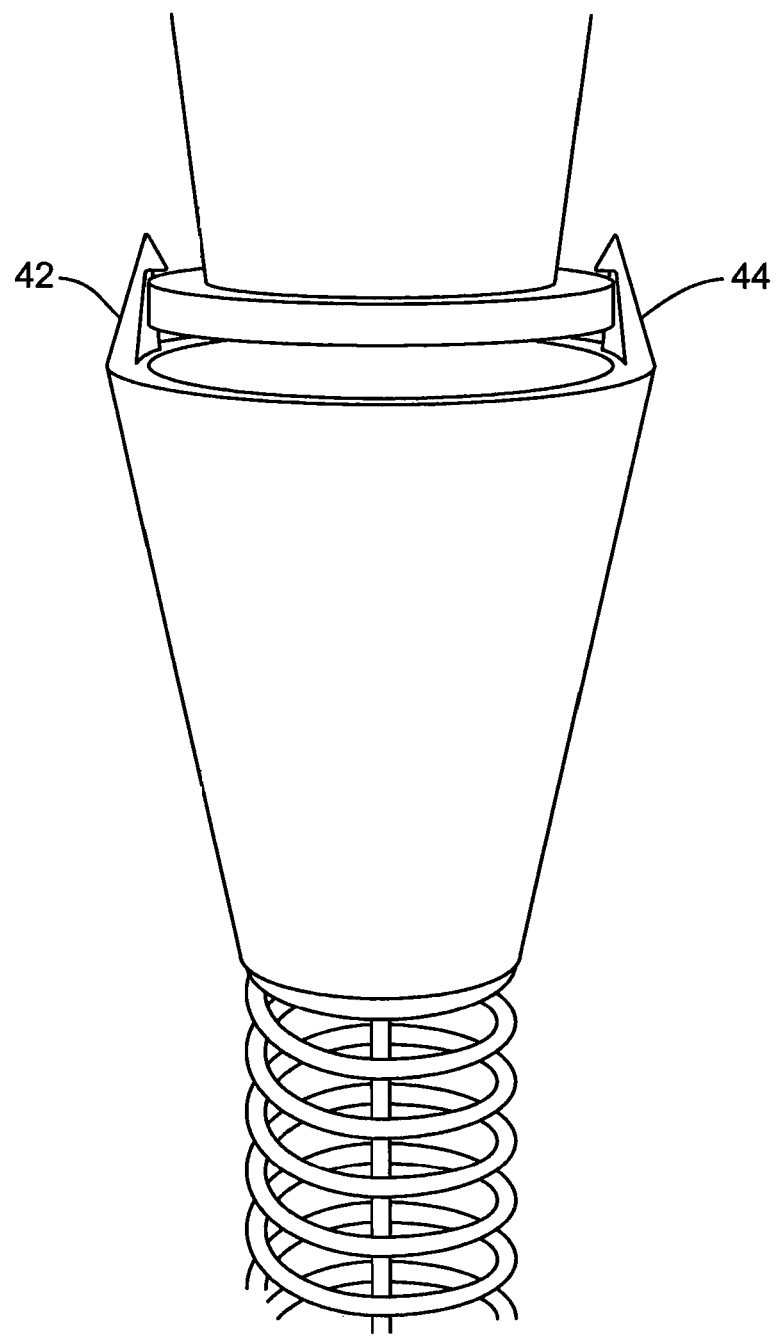
FIG. 7 is a side view illustrating the connection hub of the hypodermic needle.

FIGS. 6 and 7 show how the device 18 fits onto a hypodermic needle. A hypodermic needle 34 typically comprises a needle shaft 38 and a hub 40 which fits onto the syringe 32. The needle hub 40 typically has a tapered shape and the connecting hub of the device is provided with a frustoconical shape to allow it to be pushed over the hub of the needle. The inner surface of the connecting hub 20 has a corresponding taper angle to that of hub 40, enabling it to be held in place by friction. FIG. 7 shows the connecting hub 20 fitted over the hub of 40 a hypodermic needle; resilient hooks 42, 44 are provided at the top of the connecting hub 20 which engage with the top surface of the hypodermic needle hub 40, holding it securely in position. Any other suitable method can be used to attach the connecting hub to the needle hub including slots within the connecting hub designed to fit ridges on the needle hub. Alternatively, the connecting hub may be an integral part of the needle hub.

Figure 8:
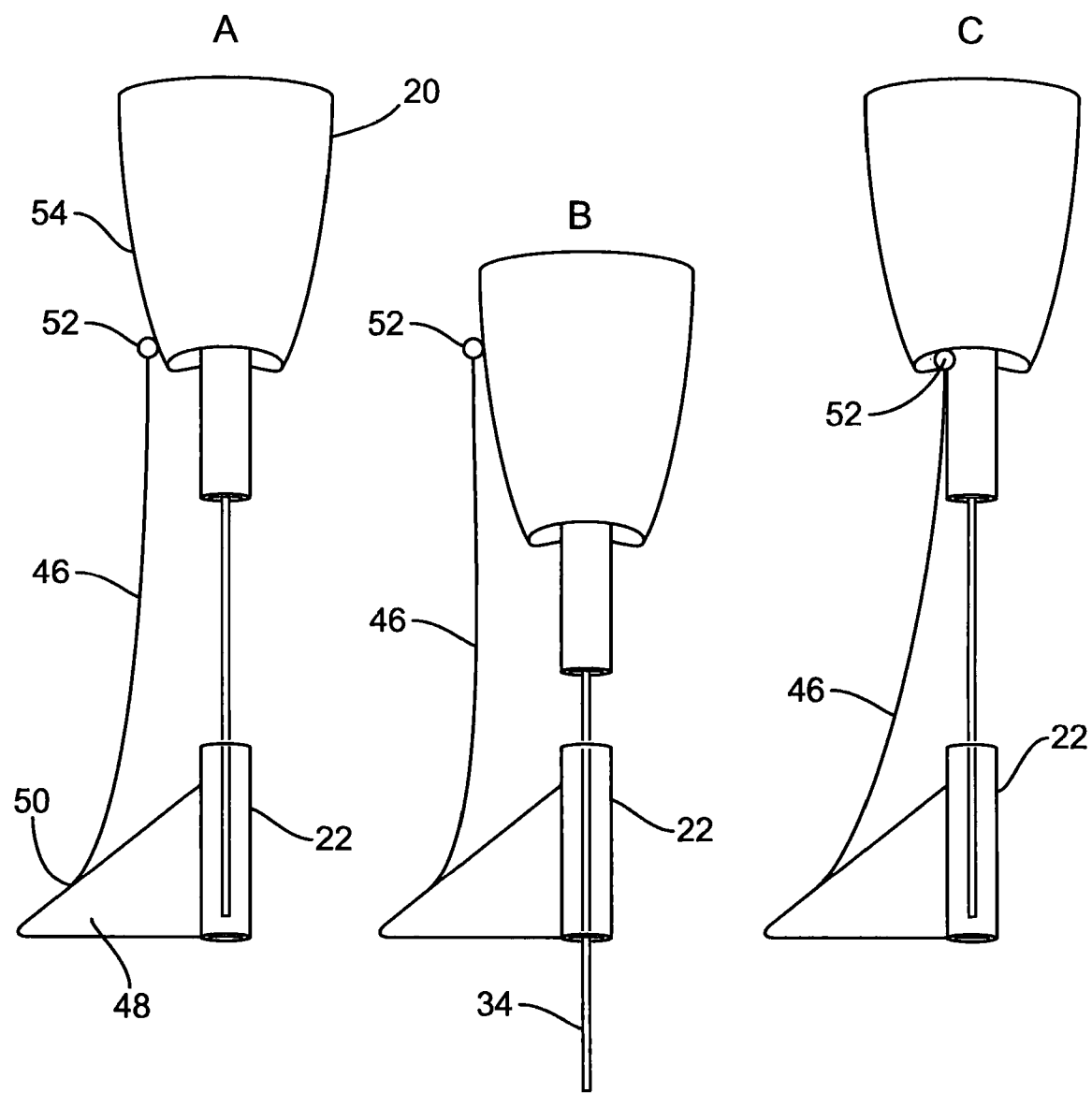
FIGS. 8A-8C illustrate the locking mechanism of the device.

The device is also provided with a safety mechanism to cover the tip of the hypodermic needle before use and to lock it in this position after use, as illustrated in FIG. 8.

FIG. 8A shows the device ready for use. The safety mechanism comprises a leaf spring 46 which is mounted onto an arm 48 extending from the sheath 22 at one end 50, with its free end 52 resting against the outside surface 54 of the connecting hub 20. The free end 52 of the leaf spring 46 has a rounded end to enable smooth travel over the surface of the connecting hub 20.

FIG. 8B shows the device in use, with the sheath 22 in its retracted position and the tip of the hypodermic needle 34 extending from the sheath 22. In this position, the free end 52 of the leaf spring 46 has travelled upwards over the surface 54 of the connecting hub 20.

FIG. 8C shows the device in its locked state. When the sheath 22 is released from its retracted position shown in FIG. 8B, it will be pushed downwards by coil spring 24 (not shown). The leaf spring 46 will similarly return to its original position as shown in FIG. 8A. From this position the leaf spring may be relocated under recessed hub as shown in FIG. 8C. Once the free end 52 of the leaf spring 46 has moved off the edge of the connecting hub 20, it will be deflected inwards and any upwards movement of the sheath 22 will push the free end 52 into the inner surface of the connecting hub 20, preventing further upwards movement and thereby preventing the sheath 22 from moving upwards sufficiently to expose the hypodermic needle 34.

Figure 9C:
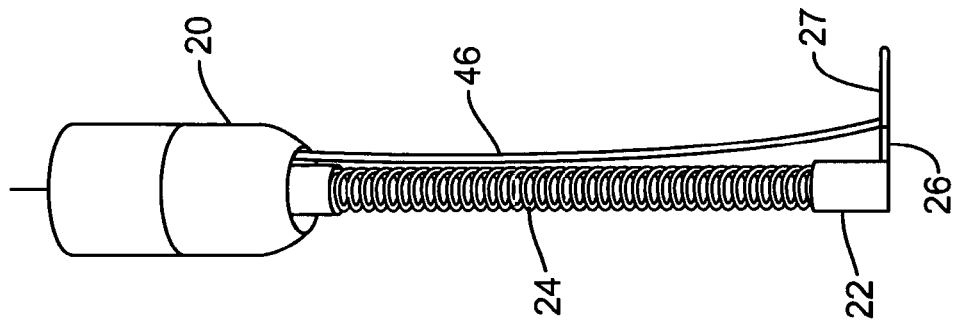
FIGS. 9A-9C illustrate a second embodiment of the locking mechanism of the device.
Figure 9B:
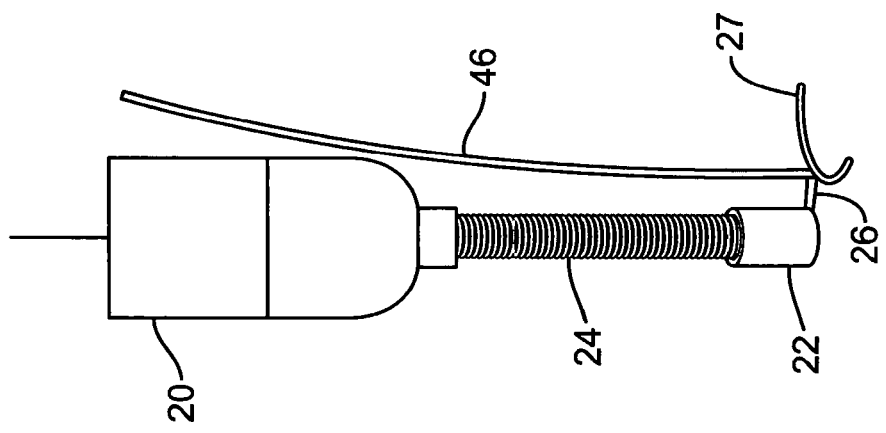
Figure 9A:
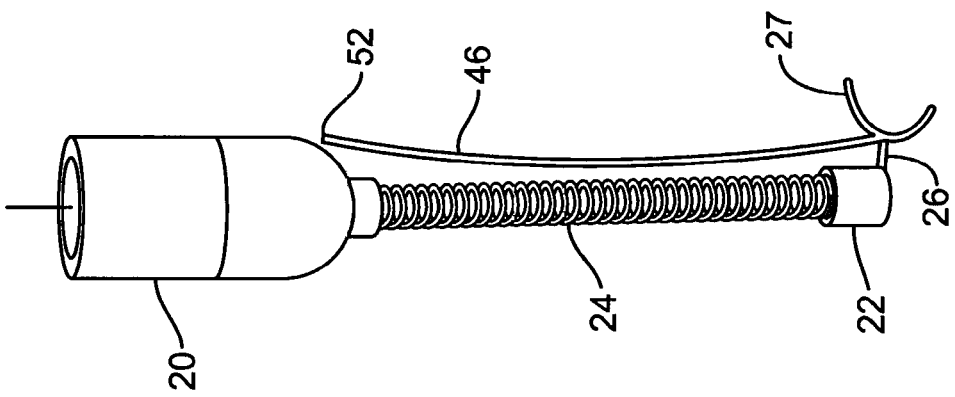

FIGS. 9A-9C shows a second embodiment of the locking device. In this embodiment, the distance gauge comprises an arm 26 attached to sheath 22, the arm 26 having a C-shaped tip 27 as described in FIGS. 5C and 5D. A leaf spring 46 is attached to arm 26, and extends upwards to form the locking mechanism. FIG. 9A shows the device in its initial position, with the free end 52 of the leaf spring 46 resting on the outside surface of the connecting hub 20; FIG. 9B shows the device in use with the spring 24 compressed and the free end of the leaf spring extending upwards against the outside surface of the connecting hub 20; and FIG. 9C shows the device in its locked state, with the free end of the leaf spring 36 located on an internal surface of the connecting hub.

A further embodiment is illustrated in FIGS. 10A-10F. FIG. 10F shows a perspective view of the device 56, with FIGS. 10A-1010D showing top, front, bottom and side views respectively and FIG. 10E showing a cross section through B-B of FIG. 10B.

The device 56 comprises a connecting hub 20 for connecting to a hub of a hypodermic needle, a sheath 22 and a pair of bow springs 58 disposed between them. As in previous embodiments, the connecting hub 20, sheath 22 and bow springs 58 are dimensioned so that when connected to a hypodermic needle, the tip of the hypodermic needle is covered by the sheath 22, when no force is applied to the bow springs 58.

As with previous embodiments, the device 56 is provided with a gauge 60 for positioning the hypodermic needle onto which the device is mounted. Distance gauge 60 may be used to both set the distance of the hypodermic needle from a fixed marker (by virtue of the distance between the concave surface of the C-shape and the central aperture of the sheath) and the angle of the hypodermic needle (by virtue of the shape of the underside surface of the gauge). Other types of gauge for setting the distance and angle of the hypodermic needle are also suitable, in particular those disclosed in other embodiments above.

The cross-sectional view of FIG. 10E shows the details of the sheath 22 in more detail. The sheath 22 comprises a channel 66 formed by a central aperture, an outer wall 62, an inner wall 64 around the channel 66 and a recess 68 defined between the inner and outer walls 64, 62. The outer surface of the inner wall is conical, with its smallest diameter at the top of the channel and tapering outwards. The outer wall is cylindrical, thereby forming a circular recess between them.

The device 56 is shown in use in FIGS. 11A and 11B, which are both cross-sectional views of the same view as FIG. 10E.

FIG. 11A shows the device 56 connected to a hypodermic needle and placed on the surface of an eye 10. No pressure has been applied against the bow springs and the device 56 is in its passive state. The needle shaft 34 can be seen in the channel 66 of the sheath 22, with its tip covered by the sheath. In use, the hypodermic needle will be pushed against the eye, compressing the bow springs so that the distance between the connecting hub 20 and sheath 22 decreases, allowing the needle shaft 34 to enter the eye 10. Although a different spring is used than the previous embodiments, the basic mechanism is the same.

FIG. 11B shows the device 56 in its locked position, in which the needle shaft 34 of the hypodermic needle is in the recess 68 between the inner and outer walls of the sheath 64, 62. In this position, any compressive force on the bow springs will not allow the needle to become unlocked.

The device is locked from the position in FIG. 11A simply by pressing on the bow springs 58 to push the sheath 22 away from connecting hub 20, thereby disengaging the needle shaft 34 out of the channel 66. A slight transverse motion of the bow springs 58 pushes the needle shaft 34 into the recess 68. The tolerance between the channel and needle shaft is small, making it difficult for the needle shaft to be accidently pushed back into the channel.

The device is suitably manufactured by injection moulding or 3D printing, although other methods could also be used.

This device provides both active and passive protection against needlestick injury. The active position is provided by the locking mechanism, which enables the sheath to be locked in place over the tip of the hypodermic needle after use. The passive position is provided by the sheath surrounding the hypodermic needle tip in normal use; the needle tip is only exposed when a force is exerted on the sheath against the biasing device and for this to occur the sheath must be resting against the body part being injected to, i.e. the eye, and the needle tip only projects from the sheath straight into the body part itself.

The device is suitable for use with a range of body parts in addition to the eye, for example subcutaneous injections. The device can be used as a locking device with or without a gauge. The gauge can be adapted for the particular use. The device is particularly suitable for targeted injections of cancer sites.

This invention has the advantage that a single device allows the location, angle and depth of injection to be set. In addition, the invention provides protection against inadvertent injury to healthcare workers and patients.

The invention claimed is:

1. A guidance device for delivering a therapeutic agent into an eye with a hypodermic needle, the guidance device comprising:

a connector for connecting the guidance device to a hypodermic needle;

a sheath that surrounds the hypodermic needle during use of the guidance device;

a biasing device between the connector and the sheath; and a distance gauge to position the hypodermic needle a set distance from a fixed location, the distance gauge comprising an arm mounted on the sheath and connected to a convex side of a C-shaped tip, wherein:

during use of the guidance device, the sheath is moveable between a first position into which the sheath is biased by the biasing device and a second position in which the sheath is retracted against the force of the biasing device;

in the first position a tip of the hypodermic needle is covered by the sheath; and in the second position a defined length of the hypodermic needle is exposed.

2. The guidance device according to claim 1, wherein the biasing device biases the sheath into the first position after use of the guidance device, thereby covering the tip of the hypodermic needle.

3. The guidance device according to claim 1, wherein an angle of the arm with respect to the sheath has a pre-defined setting to ensure the hypodermic needle enters at a correct angle into a surface to be injected on which the arm is placed.

4. The guidance device according to claim 3, wherein the angle of the arm with respect to the sheath is from 70 degrees to 90 degrees.

5. The guidance device according to claim 1, wherein the arm has a curved lower face and wherein a radius of curvature of the lower face matches a radius of curvature of a surface to be injected.

6. The guidance device according to claim 1, wherein the biasing device comprises one or more bow springs.

7. The guidance device according to claim 1, further comprising a locking mechanism that locks the sheath over the hypodermic needle after use of the guidance device.

8. The guidance device according to claim 7, wherein the sheath comprises a channel and the locking mechanism comprises a recess in the sheath, wherein in an unlocked position of the locking mechanism the hypodermic needle passes through the channel and in a locked position of the locking mechanism, the hypodermic needle rests in the recess.

9. The guidance device according to claim 1, wherein the distance gauge comprises one or more distance markers.

10. The guidance device according to claim 9, wherein the distance gauge comprises a first distance marker at an external circumference of the C-shaped tip and a second distance marker at an internal circumference of the C-shaped tip.

11. The guidance device according to claim 1, wherein the C-shaped tip is an arc having a radius of curvature substantially equal to a radius of curvature of the limbus of the eye.

12. A method for positioning a syringe with hypodermic needle for delivery of a therapeutic agent to an eye or removal of samples of tissue or fluid from the eye using a guidance device according to claim 1, the method comprising:

placing the sheath of the guidance device onto the desired position on the surface of the eye;

placing the C-shaped tip of the distance gauge of the guidance device on a fixed point on the eye to thereby set a position of the sheath;

pushing the syringe downwards so that the sheath is displaced against the biasing device from its first position relative to the hypodermic needle to its second position, while the sheath remains on the surface of the eye so that the hypodermic needle enters the eye by a predetermined distance;

injecting contents of syringe into the eye or removing samples of tissue or fluid from the eye; and removing syringe and hypodermic needle from the eye.

13. The method according to claim 12, wherein the C-shaped tip of the distance gauge is placed on the limbus of the eye.

14. The method according to claim 12, wherein the arm has a pre-defined angle with respect to the sheath, the method further comprising:

resting the arm on the surface of the eye to thereby set an angle of the sheath with respect to the surface.

15. The method according to claim 12, further comprising:

after use of the guidance device, allowing the sheath to return downwards to thereby lock the sheath in place over the hypodermic needle.

* * * * *